(12) United States Patent
Spielberg

(10) Patent No.: US 7,044,965 B1
(45) Date of Patent: May 16, 2006

(54) THERAPEUTIC CELLULAR STENT

(76) Inventor: Theodore E. Spielberg, 10 Pinewood Cir., Wellesley, MA (US) 02181

( * ) Notice: Subject to any disclaimer, the term of this patent is extended or adjusted under 35 U.S.C. 154(b) by 0 days.

(21) Appl. No.: 10/318,862

(22) Filed: Dec. 13, 2002

(51) Int. Cl.
*A61F 2/06* (2006.01)

(52) U.S. Cl. ..................... 623/1.42; 424/426

(58) Field of Classification Search ...... 623/1.15–1.48; 424/2.11, 426
See application file for complete search history.

(56) References Cited

U.S. PATENT DOCUMENTS

| | | | |
|---|---|---|---|
| 6,071,305 A * | 6/2000 | Brown et al. ............... 623/1.43 |
| 6,190,404 B1 * | 2/2001 | Palmaz et al. ............. 623/1.15 |
| 6,379,381 B1 * | 4/2002 | Hossainy et al. .......... 623/1.42 |
| 6,395,325 B1 * | 5/2002 | Hedge et al. .............. 427/2.11 |
| 2002/0007209 A1 * | 1/2002 | Scheerder et al. ......... 623/1.15 |
| 2002/0058983 A1 * | 5/2002 | Dzau et al. .................. 623/1.4 |
| 2002/0099438 A1 * | 7/2002 | Furst .......................... 623/1.16 |
| 2003/0059463 A1 * | 3/2003 | Lahtinen ..................... 424/450 |
| 2003/0060873 A1 * | 3/2003 | Gertner et al. ............. 623/1.15 |
| 2003/0120339 A1 * | 6/2003 | Banik et al. ................ 623/1.42 |
| 2003/0138950 A1 * | 7/2003 | McAllister et al. ......... 435/366 |
| 2006/0030937 A1 * | 2/2006 | Vallana et al. ............. 623/1.42 |

* cited by examiner

*Primary Examiner*—Suzette J-J Gherbi
(74) *Attorney, Agent, or Firm*—Cesari and McKenna LLP

(57) ABSTRACT

A vascular stent carries living therapeutic cellular material. The stent in widely implantable over the vascular system, and allows either localized or systemic delivery of the therapeutic products produced by the cellular material to thereby enhance patient treatment.

22 Claims, 1 Drawing Sheet

THERAPEUTIC CELLULAR STENT

BACKGROUND OF THE INVENTION

1. Field of the Invention

The invention relates to vascular stents and, more particularly, comprises a vascular stent which facilitates cellular transplant in animal bodies such as humans.

2. Background Information

Stents are commonly used to support blood vessels whose walls have been damaged or to bridge and repair vessels that have been injured. Typically, such stents consist of an expansible mesh which is collapsible during insertion into a vessel and thereafter expansible (e.g., by means of a balloon catheter) to firmly engage the inner wall surface of a blood vessel and secure it in place.

In addition to providing structural support, some stents have often been coated with various medications for such purposes as minimizing inflammation and providing treatment. Examples of commonly used stents are described in "Handbook of Coronary Stents", 2d ed., by Patrick W. Serruys and Michael J B Kutryk, Eds. (1997, 1998). In addition, some stents have been coated with vascular endothelial cells in order to promote endothelialization and thereby lessen clotting and decrease resteonsis.

It has been known to introduce living, functional animal cells into human bodies in order to remedy deficiencies in the production of necessary hormones and other body products. Usually, the cells are introduced by surgically implanting them in the peritoneal cavity, or by injecting them into the portal vein where they lodge in the liver. In the peritoneal cavity, blood vessels must grow and develop to nourish the cells and transport their therapeutic products (e.g., insulin) to the sites where they will be used. In the liver, the sinusoids provide blood, but the cells may obstruct these sinusoids, thus inducing portal hypertension and even cirrhosis of the liver. Other sites have been tried (e.g., the renal capsule); however, the lack of immediate vascular access poses problems for these approaches.

Auto transplantation of parathyroid glands that have been removed because of extensive thyroid surgery have been performed in the forearm with variable results, as has autotransplantation by way of pancreatectomy for neoplasm, where the islet cells producing insulin and/or glucagon may be preserved for autotransplantation to prevent diabetes. Other examples of autotransplantation include the use of the patients' stem cells to repair injured organs or tissue.

Microporous or semipermeable membranes have been used in connection with transplants; examples are described in U.S. Pat. Nos. 4,209,776, 5,911,704, and 5,704,910. A disadvantage to such an approach is that the pores of these membranous devices can be plugged with proteinaceous deposits. Further, the membranes also tend to increase clotting. In each case this compromises the viability of the transplanted cells and their ability to function. Also, vascular grafts or combination stent-grafts using Dacron or ePTFE increase thrombogenicity and compromise blood flow by increasing the inflammatory response with neointimal proliferation.

Stents have also been combined with heart valves, to anchor them in place. Some of these heart valves contain living cells.

SUMMARY OF THE INVENTION

Accordingly, it is an object of my invention to facilitate therapeutic cell implantation in animal bodies, especially humans.

Further, it is an object of my invention to enable therapeutic cell implantation at a wide variety of sites within a body, without major surgery.

Still another object of my invention is to facilitate therapeutic cell implantation at sites having abundant blood supply for nourishing the cells and transporting body and cell metabolites and hormones.

Yet another aspect of the invention is to efficiently provide stem cells or autologous bone marrow cells directly to areas of organ injury, to thereby facilitate repair of the injured organ.

Still a further object of this invention is to provide a means for intravascular transplantation of therapeutic cells or therapeutic cellular tissue while avoiding use of microporous or semipermeable membranes or vascular grafts and their attendant disadvantages.

In accordance with my invention, I provide a stent for engagement with the inner wall of a blood vessel, to thereby secure it in place. The stent carries living therapeutic (i.e., non-endothelial) cells for generating therapeutic products. The cells may be isolated cells that have been harvested for this purpose, or they may be part of living tissue. Examples of cells that are appropriate for this purpose are endocrine cells that produce useful metabolic products such as hormones; insulin from islet cells; heparin from mast cells; β-glucocerebrosidase for the treatment of Gaucher's disease, among others, as well as stem cells for the regeneration of organs.

The stent of the present invention provides significant flexibility in the selection of the site of implant of the cells. For example, in the case of a lesion in a vessel that must be treated, one may implant the stent at the site of the lesion, the stent in this case incorporating mast cells that enhance the secretion of heparin at the site, or stem cells or other forms of therapeutic cells where such cells have been lost due to injury. In other cases, one may choose to implant the stent (and the cells within it) at any convenient site in the body for systemic transport of cell products over a broader area or alternatively to service a particular organ. Moreover, the stent may be constructed of a biodegradable substance such as catgut or a polymer so that it disappears, leaving the transplanted cells enclosed within the blood vessel wall.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
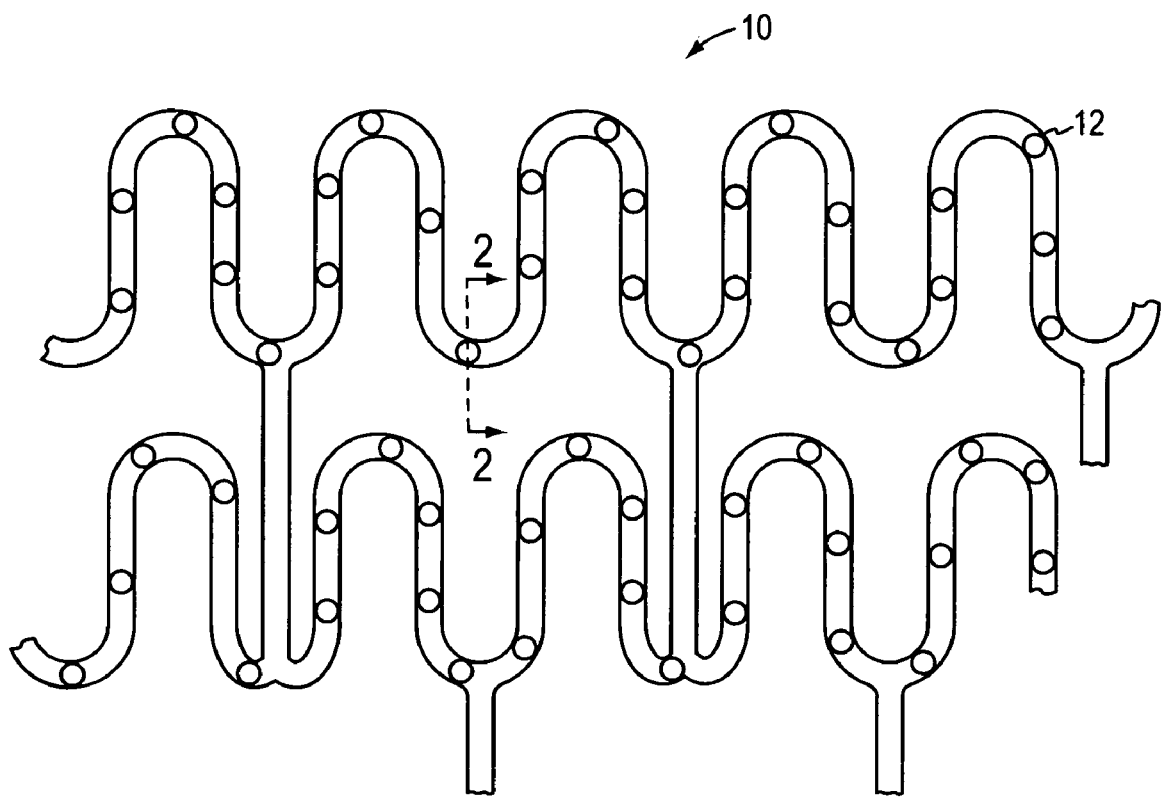
FIG. 1 is a pictorial view of a portion of one form of stent that may be used in accordance with the present invention.
Figure 2:
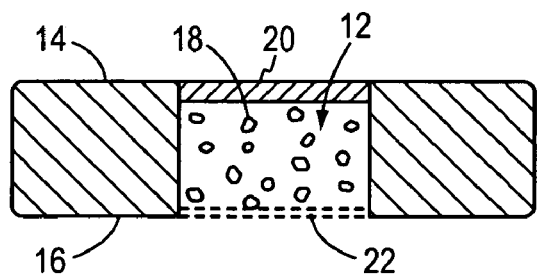
FIG. 2 is an enlarged cross-sectional view along the line 2—2 of FIG. 1 showing the cell-containing reservoir in detail.

In FIGS. 1 and 2, an illustrative stent 10 that may be used in accordance with the present invention is shown in the form of a mesh whose radial cross-section is collapsible for insertion into a blood vessel and is thereafter expansible (e.g., by inflating a balloon) into contact with the inner wall of the blood vessel to thereby secure the stent at a desired location. Stents of this general type are known in the art. As modified by the present invention, however, and as shown in cross-section in FIG. 2, a plurality of wells 12 are spaced along one or more portions of the stent and extend through the stent from an upper surface 14 to a lower surface 16. The wells carry charges of living cells 18 that are confined within the well at the upper end of the cell by a thin membrane or skin 20 of biodegradable material such as albumin or other gelatinous or protinaceous material, and at the lower end of the cell by a mesh or screen 22 of sufficient porosity to admit cell nutrients into the well while confining the cells themselves within the well.

The stent is inserted into a patient in the manner of a conventional stent, i.e., in the contracted state, and is lodged at a desired location in the vessel by expanding the stent until its outer wall 14 presses against the inner wall of the blood vessel. When this is done, the membrane 20 either ruptures or gradually degrades to bring the cells directly into contact with the vessel wall. The cells generate therapeutic products and engage in exchange of cell and body products through the blood vessel wall. Nutrients to sustain the cell pass through the mesh 22 from the blood stream, while metabolic products of the cell pass in the reverse direction into the blood stream.

The cells are living organisms that produce therapeutically-useful products for transport or diffusion thorough the membrane and/or screen and into the surrounding tissue, fluid or blood stream. The cells may advantageously produce hormones, such as insulin, parathyroid hormone, and growth hormone; anticlotting substances such as heparin; and substances such as β-glucocerebrosidase for the treatment of Gaucher's disease, a particularly debilitating disease which causes anemia and liver and splenic enlargement due to enzyme deficiency and which has heretofore required periodic injection of the enzyme at significant cost. In general, any therapeutic substance that can be manufactured by a cell may be used in the stent of the present invention. In addition, cells from the same patient may be used for autotransplantation; such as parathyroid cells when they have to be removed because of extensive thyroid surgery. Other therapeutic cells from the same patient may be harvested and grown in tissue culture beforehand (e.g. mast cells producing heparin or cells producing various growth factors) and then be reimplanted in the desired vascular location through the cellular stent.

In addition, therapeutic cells from any animal source that have been modified to prevent rejection (such as cells derived from knock out animals without MHC components) may be transplanted via the cellular stent as well as genetically modified or subjected to nuclear transfer or other means to enhance longevity and function. Moreover, any cell susceptible to rejection may be used in this cellular stent in combination with anti-rejection medications.

Figure 3:
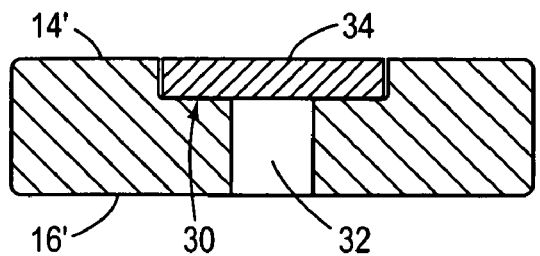
FIG. 3 is an enlarged cross-sectional view of a portion of an alternative form of cell-delivering stent in accordance with the present invention.

FIG. 3 shows an alternative embodiment of the present invention. As shown, a shallow well 30 is formed in the outer surface 14' of the stent, and connects to the inner surface 16' of the stent by means of a channel 32. A strip of tissue 34 is lodged in the well 30. As was the case with the stent of FIGS. 1 and 2, the stent is inserted into the blood vessel of a patient in collapsed form and is thereafter expanded against the inner wall of the vessel when it is positioned at the desired location. This brings the tissue segment 34 into direct contact with the vessel wall into to provide therapeutic metabolic products from the tissue specimen directly to the vessel wall. At the same time, the inner wall 16' of the stent is washed by the blood flowing through the vessel, and the tissue specimen exchanges nutrients and metabolic products with the blood through the channel 32.

Cellular tissue may be harvested from an animal source, grown in tissue culture, or assembled by adding the desired cells to adhesion peptides or proteins such as contained in extracellular matrices as well as collagen, fibronectin, and laminin. Cells may also be embedded in polymeric films, or microvelcro, creating hybrid tissue to be deployed by the stent.

Because the stent is positionable at the region at which treatment is most desired, it may also be possible to obtain useful beneficial results with configurations which position the cells or skin on the inner or side surfaces of the stent. In such a case the cells do not provide metabolic products directly to the desired site but do so through carriage by the blood in the region. Adhesives such as fibronectin may be used to adhere the cells to the stent surface. Also, the stent can advantageously be microfabricated, using the techniques of manufacturing surface topographies favorable to cell adhesion creating pillars and holes, microgrooves, cavities, bumps, microvelcro, and microcontact printing of self-attachment. Laser writing may be used for cell placement. Protein patterning and surface modification with polymers may be used. Subsequent endotheliozation would also permanently incorporate these stents into the vascular wall.

In another embodiment the stent's surface may be microfabricated, micropatterned, and microetched as above and deployed in a blood vessel without cells. In this case endogenous therapeutic cells from the patient are recruited to attach favorably to the stent surface.

The stent of the present invention provides wide latitude in placement within a body using a vascular catheter. Thus, it can provide localized treatment at the site of a lesion in a blood vessel, or can be placed at any convenient site in any convenient blood vessel for treatment of a body on a systemic level.

It will be understood that various changes can be made in the specific embodiment described and shown herein without departing from either the spirit or scope of the invention, the invention being defined specifically in the claims.

What is claimed is:

1. A stent for implantation in an animal body, said stent having an outer face for lodging against a wall of a blood vessel and an inner face for contacting blood flowing through said vessel, said stent comprising:
   a plurality of wells adapted for carrying cells, said wells extending through said outer face of said stent to said inner face of said stent;
   a first covering at said outer face of each well for confining said cells therein;
   a second covering at said inner face of each well adapted to admit nutrients into said well after implementation in the blood vessel while still confining said cells within.

2. The stent according to claim 1 wherein the first covering is adapted to degrade subsequent to implementation of said stent such that said cells are brought directly in contact with said blood vessel wall.

3. The stent according to claim 1 wherein the first covering is adapted to be permeable to products produced by said cells.

4. The stent according to claim 1 wherein the second covering is adapted to permit products produced by said cells to enter the blood stream of said blood vessel.

5. The stent according to claim 1 wherein said cells products comprise one or more products selected from the group consisting of a hormone, a metabolic substance, and a medication.

6. The stent according to claim 1 wherein the first covering comprises albumin.

7. The stent according to claim 1 wherein the second covering comprise a mesh of sufficient porosity to admit cell nutrients into the well.

8. The stent according to claim 1 wherein said cells comprise one or more types of cells selected from the group consisting of endocrine cells, islet cells, mast cells, stem cells, and parathyroid cells.

9. The stent according to claim 1 wherein said cells are disposed in a strip of cellular tissue harvested from an animal source.

10. The stent according to claim 1 wherein said cells are disposed in a strip of cellular tissue grown in tissue culture.

11. The stent according to claim 1 wherein said cells are disposed in polymeric films.

12. The stent according to claim 1 wherein said nutrients are from blood in said blood vessel and said nutrients sustain said cells after implementation.

13. A method for providing therapeutic cells in an animal body comprising the steps of:
implanting a stent in said body, said stent carrying a charge of living therapeutic cells in a plurality of wells in said stent, said wells extending through said outer face of said stent to said inner face of said stent;
retaining said cells with a first covering at said outer face of each well;
admitting nutrients into said well after implementation in said body with a second covering at said inner face of each well, said second covering also confining said cells within said well.

14. The method of claim 13 further comprising:
bringing said cells directly in contact with a blood vessel by causing said first covering to degrade subsequent to implementation of said stent in said body.

15. The method of claim 13 further comprising:
delivering products produced by said cells to said body through said first covering, said first covering permeable to said products.

16. The method of claim 13 further comprising:
permitting products produced by said cells to enter the blood stream of said blood vessel through said second covering.

17. The method of claim 13 further comprising:
selecting therapeutic cells wherein said cells produce one or more products selected from the group consisting of a hormone, a metabolic substance, and a medication.

18. The method of claim 13 further comprising:
selecting said charge of living therapeutic cells to be one or more types of cells from the group consisting of endocrine cells, islet cells, mast cells, stem cells, and parathyroid cells.

19. The method of claim 13 further comprising:
providing said charge of living therapeutic cells includes strips of cellular tissue harvested from an animal source.

20. The method of claim 13 further comprising:
providing said charge of living therapeutic cells includes strips of cellular tissue grown in tissue culture.

21. The method of claim 13 further comprising
providing said charge of living therapeutic cells includes cells disposed in a polymeric film.

22. The method of claim 13 wherein said nutrients are from blood in said blood vessel and said nutrients sustain said cells after implementation.

* * * * *